(12) United States Patent
Linn et al.

(10) Patent No.: US 11,663,426 B2
(45) Date of Patent: *May 30, 2023

(54) COMPUTER-IMPLEMENTED SYSTEM AND METHOD FOR ENTITY TRACKING AND IDENTIFICATION

(71) Applicant: Palo Alto Research Center Incorporated, Palo Alto, CA (US)

(72) Inventors: Felicia Linn, San Jose, CA (US); Ramkumar Abhishek, Menlo Park, CA (US); Ashish V. Pattekar, Cupertino, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/361,058

(22) Filed: Jun. 28, 2021

(65) Prior Publication Data

US 2021/0326546 A1 Oct. 21, 2021

Related U.S. Application Data

(63) Continuation of application No. 14/984,600, filed on Dec. 30, 2015, now Pat. No. 11,048,891.

(51) Int. Cl.
*G06K 5/00* (2006.01)
*G06K 7/10* (2006.01)

(52) U.S. Cl.
CPC ................. *G06K 7/10366* (2013.01)

(58) Field of Classification Search
CPC ............... G06Q 20/206; G06Q 20/341; G06K 17/0025; G06K 17/0029
USPC ............... 235/380, 382, 383, 462.46, 472.02
See application file for complete search history.

(56) References Cited

U.S. PATENT DOCUMENTS

| | | | |
|---|---|---|---|
| 6,876,303 B2 | 4/2005 | Reeder et al. | |
| 8,725,530 B2 | 5/2014 | Duke | |
| 11,048,891 B1 * | 6/2021 | Linn | G16H 10/60 |
| 2002/0111826 A1 | 8/2002 | Potter et al. | |
| 2002/0133379 A1 | 9/2002 | Lewis | |
| 2003/0016122 A1 | 1/2003 | Petrick | |
| 2007/0132597 A1 | 6/2007 | Rodgers | |
| 2008/0059230 A1 | 3/2008 | Manning | |
| 2008/0303638 A1 * | 12/2008 | Nguyen | G06Q 10/00 707/E17.014 |
| 2009/0171939 A1 | 7/2009 | Athsani | |
| 2012/0065989 A1 | 3/2012 | Massoumi et al. | |
| 2012/0173257 A1 | 7/2012 | Preiss | |
| 2012/0203785 A1 | 8/2012 | Awada | |

(Continued)

*Primary Examiner* — Daniel St. Cyr
(74) *Attorney, Agent, or Firm* — Krista A. Wittman

(57) ABSTRACT

A computer-implemented system and method for entity tracking and identification is provided. A tracker associated with an entity is tracked. Communication is continuously attempted between the tracker and a tracking device associated with an individual in custody of the entity. During one of the attempted communications, an absence of the tracker is determined by identifying a time of the attempted communication and applying a time threshold to the time for the attempted communication. The absence of the tracker is identified when no communication has been established with the tracking device within the time threshold. The entity is classified as missing when the absence of the tracker is determined.

20 Claims, 5 Drawing Sheets

(56) References Cited

U.S. PATENT DOCUMENTS

| | | |
|---|---|---|
| 2012/0266102 A1 | 10/2012 | Dempski |
| 2013/0085609 A1 | 4/2013 | Barker |
| 2013/0314210 A1 | 11/2013 | Schoner et al. |
| 2014/0035726 A1 | 2/2014 | Schoner et al. |
| 2014/0162692 A1 | 6/2014 | Li |
| 2015/0169915 A1 | 6/2015 | Petre |
| 2015/0195315 A1 | 7/2015 | Kidron |
| 2015/0213225 A1 | 7/2015 | Amarasingham |
| 2015/0278765 A1 | 10/2015 | Dantuluri |
| 2015/0310508 A1 | 10/2015 | Pattekar |
| 2017/0004442 A1 | 1/2017 | Luke et al. |

\* cited by examiner

COMPUTER-IMPLEMENTED SYSTEM AND METHOD FOR ENTITY TRACKING AND IDENTIFICATION

CROSS-REFERENCE TO RELATED APPLICATION

This application is a continuation of U.S. Pat. No. 11,048,891, issued Jun. 29, 2021, the priority date of which is claimed and the disclosure of which is incorporated by reference.

FIELD

This application relates in general to tracking entities, and in particular to a computer-implemented system and method for tracking and authenticating interactions.

BACKGROUND

In many professions and industries, companies and individuals are tasked with the care and tracking of individuals or objects. For instance, in the medical field, caretakers are responsible for the care and whereabouts of a patient, including the transfer of a patient from one caretaker to another. In one example, an ambulance is called for an injured patient and upon arrival, an emergency medical technician assumes care of the patient during an initial evaluation and a ride to the hospital. Once at the hospital, the patient is then placed in the care of an emergency room technician, and later, may be placed in the care of a doctor for treatment. Similarly, jails, prisons, and detention facilities are generally required to ensure the whereabouts of prisoners.

Further, in other industries, objects require tracking and possibly, authentication. For instance, in the medical field, the transfer of transplant organs require careful monitoring and transportation to prevent loss of the organs, which can be fatal to a patient. Likewise, in the financial or legal field, the transfer or movement of documents require accurate tracking to ensure that a chain of custody is properly followed, which may be used in court proceedings. Additionally, the tracking of expensive items or non-replaceable artifacts moved within and across various fields is important to ensure delivery of the object in an efficient and safe manner.

Conventional methods for tracking individuals and objects exist. With respect to medical patients, manual tracking relies on each of the medical professionals tasked with care of the patient to ensure the patient's whereabouts. Currently, manual patient tracking includes physically monitoring a patient's location and subsequently, a physical handoff of the patient, as well as the patient information, such as medical history, condition, and vital sign measurements. For example, when a patient is transferred from one medical professional to another, such as from an EMT to an emergency room (ER) worker or triage nurse, any information collected by the EMT regarding the patient is provided to the ER worker or triage nurse to facilitate care and assist with a diagnosis. Unfortunately, relying only on the caretakers for manual tracking of the patient, including the tracking of patient information, is unreliable as data collected for the patient is frequently lost during the transition due to the amount of time required and nature of the emergency, which can result in misdiagnoses and inadequate care. Further, monitoring of patient information, such as vital information can be automated using wearable monitoring devices, such as a Fitbit device, by Fitbit Inc. or an Apple watch by Apple Inc. However, the data is maintained and made accessible only to the patient and can be difficult to transfer to the medical care professionals depending on the patient's condition. Further, conventional monitoring devices merely track information about the patient and fail to monitor interactions involving the patient, such as patient transfers.

Further, conventional methods to track objects, such as mail, include utilizing scannable tags, such as bar codes. Specifically, a unique bar code is attached to each individual mail item. The bar code is then scanned upon arrival at a mail facility and at every intermediate destination until the final destination is reached. However, individually scanning each piece of mail can be extremely time consuming and costly. Further, if a mail item becomes lost, the only available information is a location at which the mail item was last scanned and no information is provided about any individuals responsible for the mail item to assist in locating the missing item. Alternatively, human couriers are used to personally transport an object from one location to another. However, there is no guarantee that the courier will not lose the transported object and the only information available for helping to find the object is the human courier, who may be at fault.

Therefore, there is a need for an approach to effectively and accurately track entities, as well as interactions involving the entities, to reduce an amount of time required for entity transfer and to prevent loss and ensure successful delivery of the entity. Preferably, information about each interaction is recorded for later access and display.

SUMMARY

To carefully monitor entities and ensure successful transfer of the entities, real-time tracking can be utilized to track interactions involving an entity and authenticate parties responsible for the entity. Specifically, a tracking device is associated with each individual responsible for an entity. A tracker can optionally be associated with the entity. Interactions between two or more individuals or between an individual and an object can be tracked via the tracking device. An interaction between individuals can occur during the transfer of an entity from one of the individuals to the other. In addition to the physical transfer of the object, information about the object can be transferred from the tracking device of the transferring individual to the tracking device of a recipient individual. Further, the transferred information can be added to a record for the entity in real-time or at a later time.

Further, for tracking interactions between individuals and objects, the object can be associated with a tracker, while the individual is associated with the tracking device. The tracking device can read the tracker to determine a presence of the object associated with that tracker continuously, randomly, or at predetermined time intervals to ensure that the object is in the presence of the individual. Further, information is collected for each interaction identified between the individual and object. The information can then be stored in a record for the object for identifying the whereabouts of the object and particular individuals responsible for the object.

An embodiment provides a computer-implemented system and method for entity tracking and identification. A tracker associated with an entity is tracked. Communication is continuously attempted between the tracker and a tracking device associated with an individual in custody of the entity. During one of the attempted communications, an absence of the tracker is determined by identifying a time of the attempted communication and applying a time threshold to the time for the attempted communication. The absence of the tracker is identified when no communication has been established with the tracking device within the time threshold. The entity is classified as missing when the absence of the tracker is determined.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Caring for a person or object often requires a transfer of that person or object, such as from one individual to another. For example, in a medical setting, patients are often transferred from one caretaker to another. However, using conventional methods of tracking and transferring patients, important patient information is frequently lost and can affect the level of care provided to the patient. Further, objects, such as mail or couriered packages, are transferred from one courier to another, perhaps across country, beginning from a point of origin to a final destination. Currently, object tracking can occur via a tracking code, such as a bar code. However, the bar codes only provide information when scanned, and if an object is lost, the existing information is likely insufficient to help locate the lost object. Thus, the failure to accurately and completely provide information about the tracked entity, especially during transfer, can result in a loss of data, which is helpful to locate and maintain the whereabouts of the tracked object. To prevent data loss and increase efficiency during transfer of an entity, automated tracking and authentication of interactions can be performed.

Figure 1:
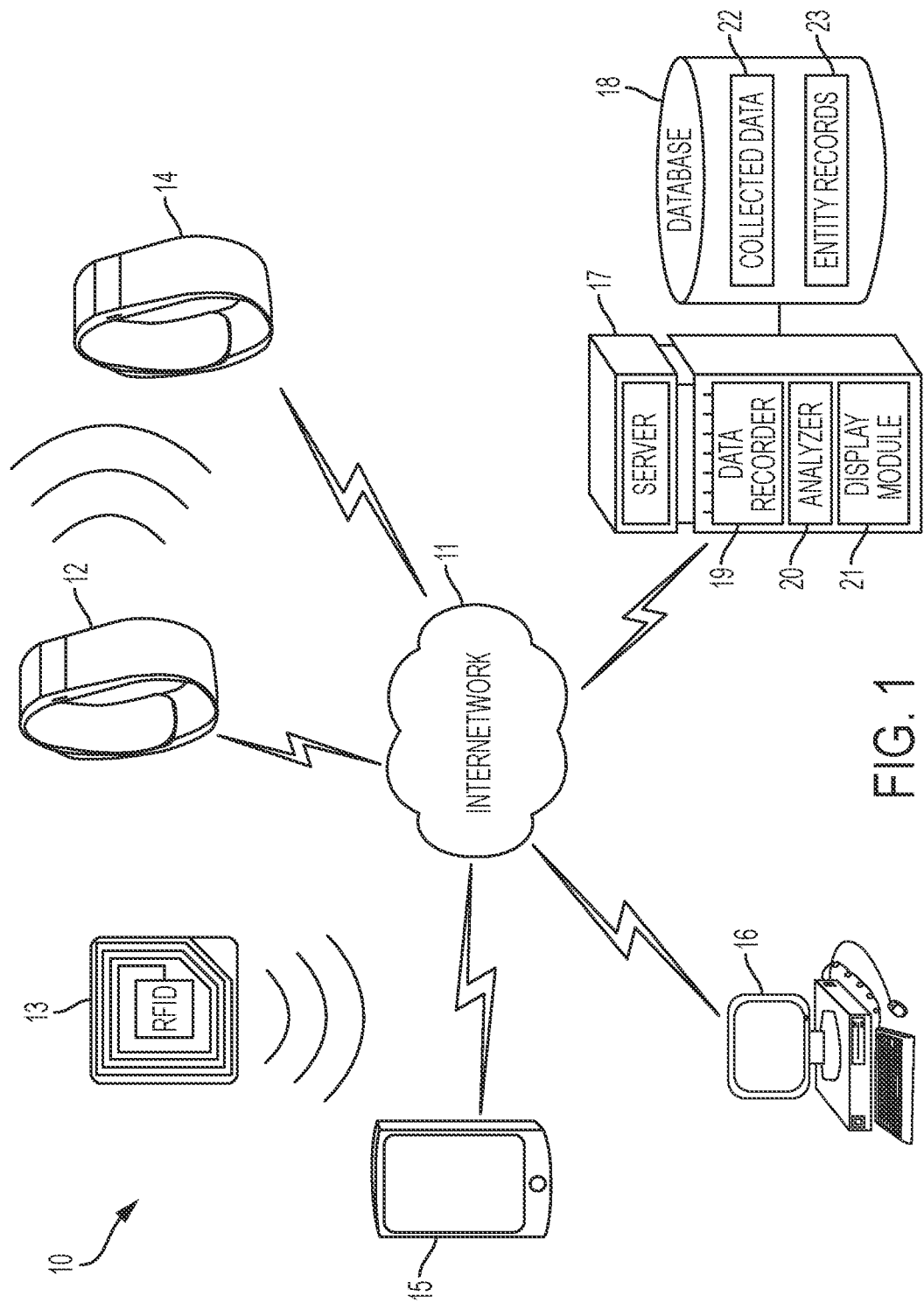
FIG. 1 is a block diagram showing a computer-implemented system for tracking and authenticating interactions, in accordance with one embodiment.

Additionally, automated tracking can increase a level of care of a tracked individual or object by generating a record of collected information that can be used to provide data about the entity or assist in locating lost entities. FIG. 1 is a block diagram showing a computer-implemented system 10 for tracking and authenticating interactions, in accordance with one embodiment. A tracker 12, 13 is associated with an entity, such as an individual or an object, to be tracked. The tracker 12, 13 can include a wearable wireless device, such as a bracelet or watch, as well as an RFID chip that can be attached to the entity, such as by adhesive, including glue, rubber, or hook and loop material. Further, a party responsible for the entity to be tracked is associated with a tracking device 14, 15, such as a wireless handheld device or a wearable wireless device, including a bracelet, watch, wristband, or glasses with embedded electronics, such as Google Glass, by Google Inc. The wireless handheld device 15 can include a standalone tracking device (not shown), a tablet (now shown), or cell phone. The tracker 12, 13 and tracking device 14, 15 can communicate wirelessly via Wi-Fi, Bluetooth, or radio frequency energy. In one embodiment, the tracker and tracking device can communicate actively, whereas in a further embodiment, the communication can occur passively. For example, two or more mobile wireless devices, one acting as a tracker and the other as a tracking device, can actively communicate. Alternatively, an RFID tracker can passively communicate with a tracking device.

The tracking device 14, 15 can include a transmitter to send information or a request to another tracking device or a tracker, a receiver to receive information from another tracking device or tracker, memory, a processor, a proximity sensor, a location sensor, such as GPS, a camera, a microphone, and a video recorder, as well as other components. Meanwhile, a tracker 12, 13, such as a wireless device, can include a transmitter, a receiver, memory, a processor, and can be connected to one or more sensors for determining and recording vital signs of a wearer. Other types of trackers, such as an RFID tag, can be passive and may only include an antenna and memory.

Interactions between individuals or between an individual and an object is identified when communication occurs between two or more tracking devices of the individuals or between a tracking device and a tracker of the object, respectively. For example, when the tracker includes an RFID chip, each tracking device can include an antenna to respectively identify the tracker, if located within a predetermined range of the tracking device and a reader system to process identification information of the tracker, such as tracker ID number and other data associated with the tracker, including information about the object. Further, communication between two or more tracking devices can occur when the devices are within a predetermined range of one another.

During a transfer interaction, an individual responsible for the entity transfers the entity to another individual and a tracking device of the responsible individual transfers information collected for the entity to the tracking device of the other individual. Also, while the entity is in the custody of a responsible party, a presence of an entity can be checked continuously, randomly, or on a predetermined basis by initiating communication between the tracking device of the responsible party and the entity tracker. Further, the entity can be tracked by ensuring the entity is within a specified range of the responsible party using the proximity sensor. Once within the specified range, communication between the devices automatically occurs.

During each interaction, information about the entity and details of the interaction can be collected. The information can be collected by either the tracker or the tracking device. For instance, in the medical field, the tracker or tracking device can perform at least one of recording vital signs of a patient, receiving speech input from the patient or the caretaker about the patient, and recording video of the patient or any interaction between the patient and the caretaker. The collected information can then be transferred, automatically or upon request, to a tracking device of an individual assuming responsible for the entity. Further, the identity of the entity or responsible party can be authenticated based on the information transferred.

Additionally, the information collected for the entity can be transmitted, not only to another tracking device, but to a data server 17 via an internetwork 11, such as the Internet. The information transfer can occur in real-time, randomly, or periodically. The data server 17 includes a data recorder 19, analyzer 20, and display module 21. The data recorder 19 receives the collected data 22 and stores the data in a database 18 interconnected to the server 17. The analyzer 20 identifies the data associated with each entity and stores the collected data in a record 23 for that entity. The analyzer 20 also analyzes the data to generate chains of custody, charts and graphs, as well as other types of data displays. The display module 21 receives requests for displaying the data 22 associated with one or more entity records and provides the data for display. Users can access the data to retrace a path of an entity in an attempt to locate the entity, to locate a particular individual responsible for the entity at a particular time or at a particular location, and to receive real-time information about the entity.

An individual can access the entity information via a computing device, such as a desktop computer 16, a laptop or tablet (not shown), or a mobile computing device 15. The requesting individual can include a medical worker treating a patient entity or a worker for a shipping service delivering a package. Other types of individuals are possible. Once made, the request is transmitted to the server 17, which obtains the request information for providing to the requesting device 16.

The client and server can each include one or more modules for carrying out the embodiments disclosed herein. The modules can be implemented as a computer program or procedure written as source code in a conventional programming language and is presented for execution by the central processing unit as object or byte code. Alternatively, the modules could also be implemented in hardware, either as integrated circuitry or burned into read-only memory components, and each of the client and server can act as a specialized computer. For instance, when the modules are implemented as hardware, that particular hardware is specialized to perform the data quality assessment and other computers cannot be used. Additionally, when the modules are stored into read-only memory components, the computer storing the read-only memory becomes specialized to perform the data quality assessment that other computers cannot. The various implementations of the source code and object and byte codes can be held on a computer-readable storage medium, such as a floppy disk, hard drive, digital video disk (DVD), random access memory (RAM), read-only memory (ROM) and similar storage mediums. Other types of modules and module functions are possible, as well as other physical hardware components.

Figure 2:
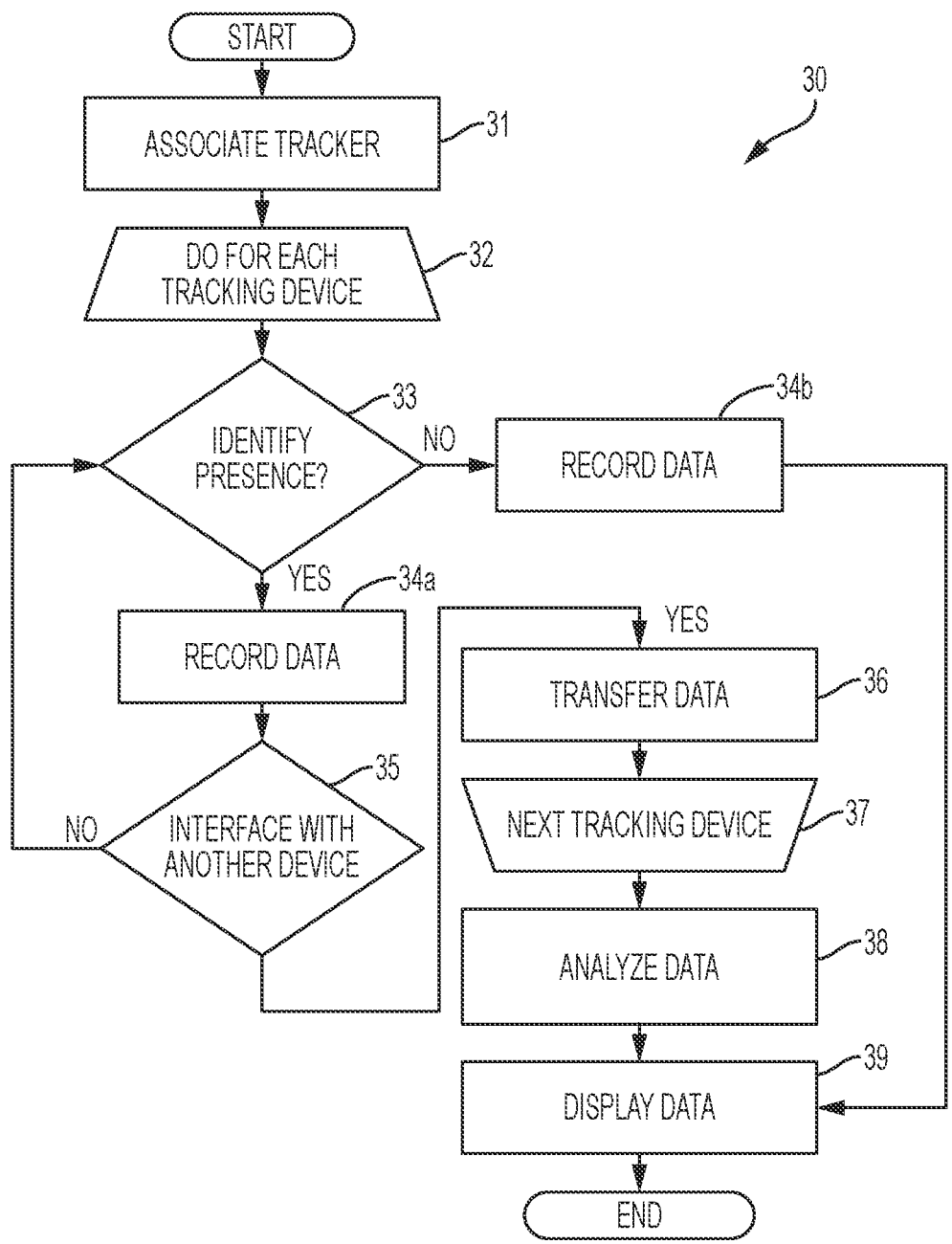
FIG. 2 is a flow diagram showing a computer-implemented method for tracking and authenticating interactions identifying attributes for anonymization, in accordance with one embodiment.

Real time tracking of entities, including interactions or transfers involving the entities, provides increased knowledge about the entity and ensures that entity data is also transferred accurately and completely. FIG. 2 is a flow diagram showing a computer-implemented method for tracking and authenticating entity interactions, in accordance with one embodiment. During tracking, interactions between parties responsible for an entity can occur, as well as interactions between a responsible party and the entity. Each interaction can include a communication attempt between the responsible parties or between a responsible party and the entity. To perform the tracking, a tracker is associated (block 31) with an entity to be tracked by affixing the tracker to the entity. For example, a wearable wireless device tracker can be secured around the wrist or neck of a human entity, while an RFID tag can be attached to an object, such as a package or envelope.

Meanwhile, a party responsible for the entity can be associated with a tracking device that communicates with the tracker or with a tracking device of another responsible party during an interaction. The tracking device can be a handheld device, or worn or affixed to a clothing garment or body part of the wearer. For each tracking device (block 32) associated with an individual tasked with caring for the entity, a presence or absence of the entity's tracker can be identified (block 33) at one of predetermined times, periodically, or at agreed upon time periods while the entity is in the care of that individual. When a presence is determined, the entity is understood to be under the control of the responsible party. However, if an absence of the tracker is determined, the entity may no longer in the care of the responsible party and may be lost.

A presence or absence of the tracker can be determined via physical contact between the tracker and a tracking device or wirelessly, such as via WiFi or Bluetooth. For instance, a connection can be established between two wearable wireless devices, one acting as a tracker and the other as a tracking device, when the wearable wireless devices are within a particular range of one another. The range can vary, but generally has a limit of about two feet to ensure that the tracking device only communicates with the tracker of the appropriate tracked entity. Similarly, when the tracker is an RFID chip, a tracking device can establish communication with the chip by reading information stored on the RFID chip. Depending on whether the tracker RFID chip is active or passive, the range of communication can vary from around one to 300 feet. However, shorter ranges are preferred to ensure that the tracking device communicates only with the tracked entity. Short range communication can occur, for example, using Near-Field Communications (NFC) devices that work over a reduced range of a few inches, or low-power bluetooth that can work over a range of a few feet.

When communication can be detected, a presence of the entity is determined. In contrast, an absence or loss of the tracker is identified when the tracking device cannot make a connection with the tracker, perhaps, because the tracker is outside the range of the tracking device. In one embodiment, an absence of the tracker is determined based on a threshold. For instance, a predetermined threshold of time for establishing communication is applied to the time during which a tracking device attempts to establish communication with a tracker. If the time to establish communication exceeds the threshold, an absence of the tracker is identified. Data about the interaction or lack of interaction between the tracking device and entity can be collected (block 34a-b), including an identity of the entity, the individual associated with the tracking device, a date and time of the communication attempt, and a location of the entity at the time of the communication attempt. Other data regarding the interaction can also be collected.

If an absence is identified, any information collected (block 34b) about the communication attempt can be stored on the tracking device and transmitted to a data server for storage in a record for the entity. Once the data is collected, the real-time tracking ends. Subsequently, the entity record can optionally be accessed (block 39) to help identify a location of the entity, such as by using the last recorded information for the entity. However, if the tracker is identified, the entity associated with the tracker is still within the care of the responsible party and the collected information (block 34a) can be recorded via one or both of the tracker and the tracking device. The interaction data collected can be stored on the tracking device, as well as transferred to a data server for inclusion in the entity record, in real-time, at predetermined time periods, or randomly.

Further, in addition to the interaction data collected, the tracking device can receive data specific to the entity tracked. For instance, during the real-time tracking of a patient entity, the tracker can record vital signs of the patient and data collected from the patient's caretaker, including information about the patient's mental state or consumption of food or drink, as well as other types of information. The entity information can be transferred from the tracker to the tracking device during an established communication. Simultaneous to or at a different time, the entity information can also be transmitted to a data server for storage and access by authorized individuals.

Additionally, during real-time tracking, the tracking device itself can record information that can be transmitted to the data server with the interaction data and entity data. Returning to the example above, the tracking device can also record vital sign information for a patient, as well as notes from the responsible party about the patient. The entity information can be stored on the tracking device until transmitted to a data server for inclusion in the entity's record, in in real-time, randomly, as requested, or at predetermined times. Collection of the entity information by the tracker or the tracking device can occur at predetermined time periods, upon request, or randomly, as well as at other time periods. In one embodiment, data recordation begins upon transfer of the entity to the responsible party's care and ends upon transfer of the entity out of the responsible party's care.

At some point during the real-time tracking, the responsible party can interact with another responsible party to whom the entity will be transferred. During the interaction, the tracking device of the responsible party may communicate with a tracking device of the new responsible party by interfacing (block 35) to the further tracking device. The interface can occur via physical contact of the tracking devices or via wireless communication, such as Wi-Fi or Bluetooth. When the tracking devices are within a predetermined range of one another, they can communicate wirelessly, and when one the tracking devices make physical contact, communication can occur. If no interface of the tracking device is identified with another tracking device, the current tracking device continues to monitor the tracker and entity by periodically continuing to check (block 33) for a presence or absence of the tracker and record or collect (block 34) data, such as interaction data and entity data.

However, if the tracking device interfaces with a further tracking device, data collected or received by the tracking device, such as the interaction and entity data, is transferred (block 36) to the other tracking device. Interfacing between two or more tracking devices can occur upon transfer of the entity. For example, during transfer of an entity from one responsible party to another, the tracking device associated with the current responsible party interfaces with the tracking device associated with the other responsible party to whom the entity is being transferred. Once the tracker has been transferred with the interaction and entity data, the tracking device (block 37) of the new responsible party periodically or randomly checks (block 33) for a presence or absence of the entity via the tracker and records (block 34) data for the entity when a presence is determined.

The interaction and entity data collected from and by each tracking device associated with the parties responsible for the entity can be analyzed (block 38) and displayed (block 39), such as via the entity's record. Analysis of the data can include generating lists, calculating averages, means, or other measurements of the data, as well as graphing the data, which is further described below with reference to FIG. 5. An individual or party responsible for or associated with the entity can access the information via a computing device for display. For example, a patient entity can access the data as a review of their medical record, while a doctor can access the data to determine how best to treat the patient entity, if necessary. Data recorded for a package can help a recipient identify when and where the package may have been damaged or a reason for delay of the package, and can help a sender determine when the package will be delivered, including any delays. Also, the data recorded for a package can be analyzed with other packages to determine an average delivery time and speed of each transfer station. Other uses of the data are possible.

Figure 3:
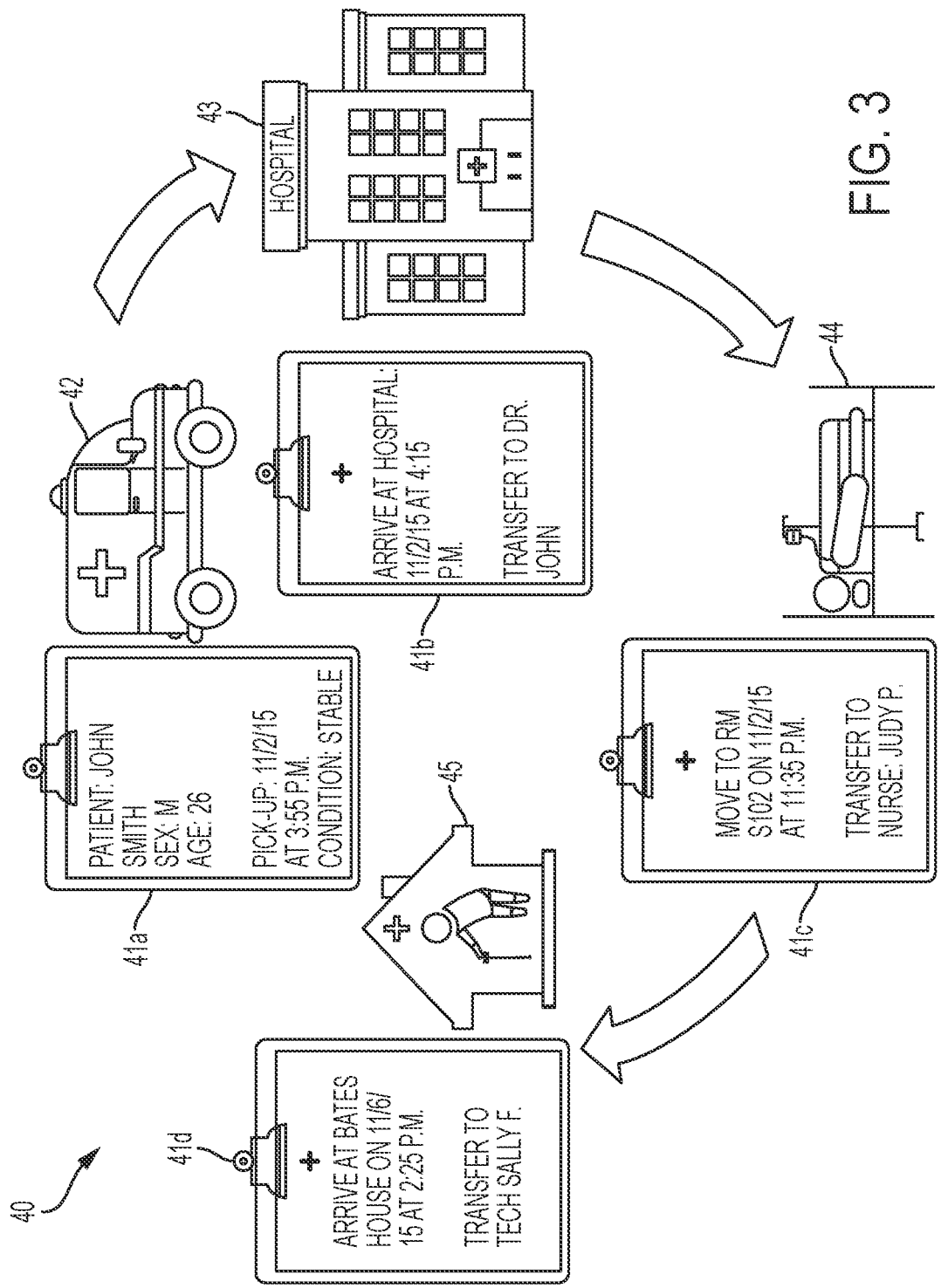
FIG. 3 is a flow diagram showing, by way of example, a process for patient tracking and authentication.

The real-time tracking system can be used for any type of entity, including individuals and objects. However, based on the type of entity tracked, the tracker used, as well as the information collected for the entity and any interactions, can differ. For instance, for individuals, such as patients or prison inmates, an active tracker may be preferred to obtain information from the individual, such as vital sign measurements, or alternatively, no tracker can be used since the tracking device of the responsible party can record voice and other actions of the individual, which can be provided by the individual or the responsible party. FIG. 3 is a flow diagram showing, by way of example, a process 40 for patient tracking and authentication. In this example, a patient collapses at work and an ambulance 42 is called. An emergency responder arrives and is wearing a tracking device, such as a pair of Google Glass glasses. Upon arrival, the emergency responder assumes responsibility of the patient by attending to and eventually loading the patient on the ambulance, if necessary.

Attending to the patient can include data 41a gathering, such as collecting information about the patient and providing medical attention. For example, the emergency responder can take vital sign measurements of the patient, talk to and ask questions of the patient, and assess the patient's condition, as well as perform one or more medical procedures. Other actions can also be taken by the emergency responder. The tracking device of the emergency responder can collect the data by recording video of the interaction between the emergency responder and the patient and recording voice input from the emergency responder or patient, such as any speech communicated between the emergency responder and patient, the patient's vital sign measurements read out by the emergency responder, and the patient's condition spoken by the emergency responder.

During an initial examination of the patient, limited information about the patient may be available. However, further information can be recorded into the tracking device as further interactions between the patient and emergency responder occur. These interactions can include observations by the emergency responder regarding the patient's physical state or the environment where the emergency situation occurred, any vital signs or other measurements about the patient that were recorded by the responder, and ongoing clinically relevant information that the responder may wish to record about the patient so that the relevant information can be made available at the hospital to help with appropriate decision making by the hospital team regarding any specific course of action to follow in order to treat the patient. Any data received by the tracking device can be stored on the tracking device, as well as transmitted to a data server for storage and entry into a record for the patient. Transmission of the data can occur in real-time or periodically, such as randomly, at predetermined times, or as requested. In a further embodiment, the transmitted data can be displayed in real-time for a user of the tracking system, such as a doctor or nurse waiting for the patient to arrive at a hospital.

Further, patient data 41*a* can also be collected by a tracker worn or attached to the patient. The tracker can wirelessly communicate with the tracking device of the emergency responder. For example, the tracker can obtain the vital signs of a patient and then transfer the data to the tracking device via Bluetooth or WiFi, as well as other means of wireless communication. Subsequently, upon receipt of the patient data from the tracker, the tracking device can store the information and transmit the information to the server, periodically or in real-time.

When the patient reaches the hospital, the emergency responder must turn responsibility of the patient over to a hospital employee, such as an emergency room doctor 43, and provide a summary of the patient's condition to allow the emergency room doctor to best treat the patient. Generally, patient information is verbally transmitted from the emergency responder, who may have written notes regarding the patient, to the emergency room doctor. However, to save time required for verbally providing the patient data to the doctor and to maintain accuracy of the data, the information can be wirelessly transferred from the tracking device of the emergency responder to a tracking device worn by the emergency room doctor.

The data transfer can occur when the emergency responder and emergency room doctor are standing within a predetermined range to one another, such as while they are briefly discussing the patient. When the tracking devices are within range, the tracking device worn by the emergency responder interfaces with the tracking device worn by the emergency room doctor and transfers the collected patient data. In one embodiment, the predetermined range is a maximum of approximately 2 meters to initiate data transfer.

The interaction, or transfer, between the emergency responder and the emergency room doctor can be authenticated to ensure that custody of the patient is transferred from and to the appropriate parties. Specifically, the authentication is based on metadata provided by each of the tracking devices worn by the emergency responder and the emergency room doctor. For instance, prior to usage, the emergency responder and emergency room doctor can register their respective tracking devices with the real-time tracking system using wearer data, such as name, address, phone number, age, job position, sex, and other identifying information. During the transfer of patient data, the wearer data from the transmitting tracking device and receiving tracking device can be exchanged and transmitted to the data server for verification. For instance, upon receipt of the wearer data from the tracking device of the emergency room nurse or doctor, the data can be confirmed or disputed. If the data indicates that the wearer is indeed a doctor that is employed at the hospital, then an identity of the doctor is confirmed.

Additionally, transfer data is recorded and stored. The transfer data includes information about the interaction or transfer, such as the transferring party and the receiving party, identification of the tracking devices associated with each of the parties, and date, time and location of the transfer. Other transfer data is possible. The transfer data can be recorded by either the tracking device of the transferring party or the receiving party for storage, as well as for transfer to a data server for inclusion in the patient's record. Once the patient and the patient data has been transferred and the transfer has been authenticated, the emergency room doctor is now responsible for the patient.

After assuming responsibility, the emergency room doctor, can access the patient data 41*a* received from the emergency responder and add to the data 41*a* by taking further vital measurements 41*b* or recording any assessments 41*b* and the patient's condition 41*b*. From the emergency room 43, the patient may be transferred to a nurse for care in a hospital room 44. To effect the transfer, the nurse picks up the patient, perhaps from the emergency room, and receives a transfer of patient data 41*a-b* from the tracking device of the emergency room doctor to a tracking device worn by the nurse. Further, interaction data is collected from the transfer or interaction between the emergency room doctor and nurse. While caring for the patient, data 41*c* collected by the nurse can be added to the patient data 41*a-b* provided by the emergency room doctor and emergency responder. Also, during the patient's hospital stay, one or more transfers between nurses, such as upon a shift change, can occur (not shown) and data from each of the responsible nurses can be collected and stored.

Upon the patient's discharge from the hospital 44, the patient may be admitted to an assisted living facility 45 to complete recovery. The nurse can release the patient into the care of an employee for the assisted living facility and a transfer of data 41*a-c* can occur wirelessly between the nurse's tracking device and a tracking device worn by the assisted living facility employee during transfer of the patient. Further, data about the interaction between the nurse and the assisted living facility employees can be collected and added to the other interaction data for the patient. The transferred patient data 41*a-c* and interaction data provides the assisted living facility with a complete overview of the patient and his medical history up to date, including from the time the patient was assisted by the emergency responder, as well as the parties responsible for caring for the patient. Further, the assisted living facility employee, as well as other employees can add to the information during the patient's stay, including updates regarding the patient's health, improvements, vital signs, and other types of information. In one embodiment, tracking continues as long as the patient remains in the care of another. For example, upon release of the patient from the assisted living facility to his house, the tracking can terminate and if the patient is wearing a tracker, the tracker can be returned. Alternatively, the patient can continue to be tracked and monitored upon leaving the assisted living facility. Other examples of tracking patient interactions are possible. Also, other examples of tracking individual interactions, such as the transfer of prison inmates, are possible.

Figure 4:
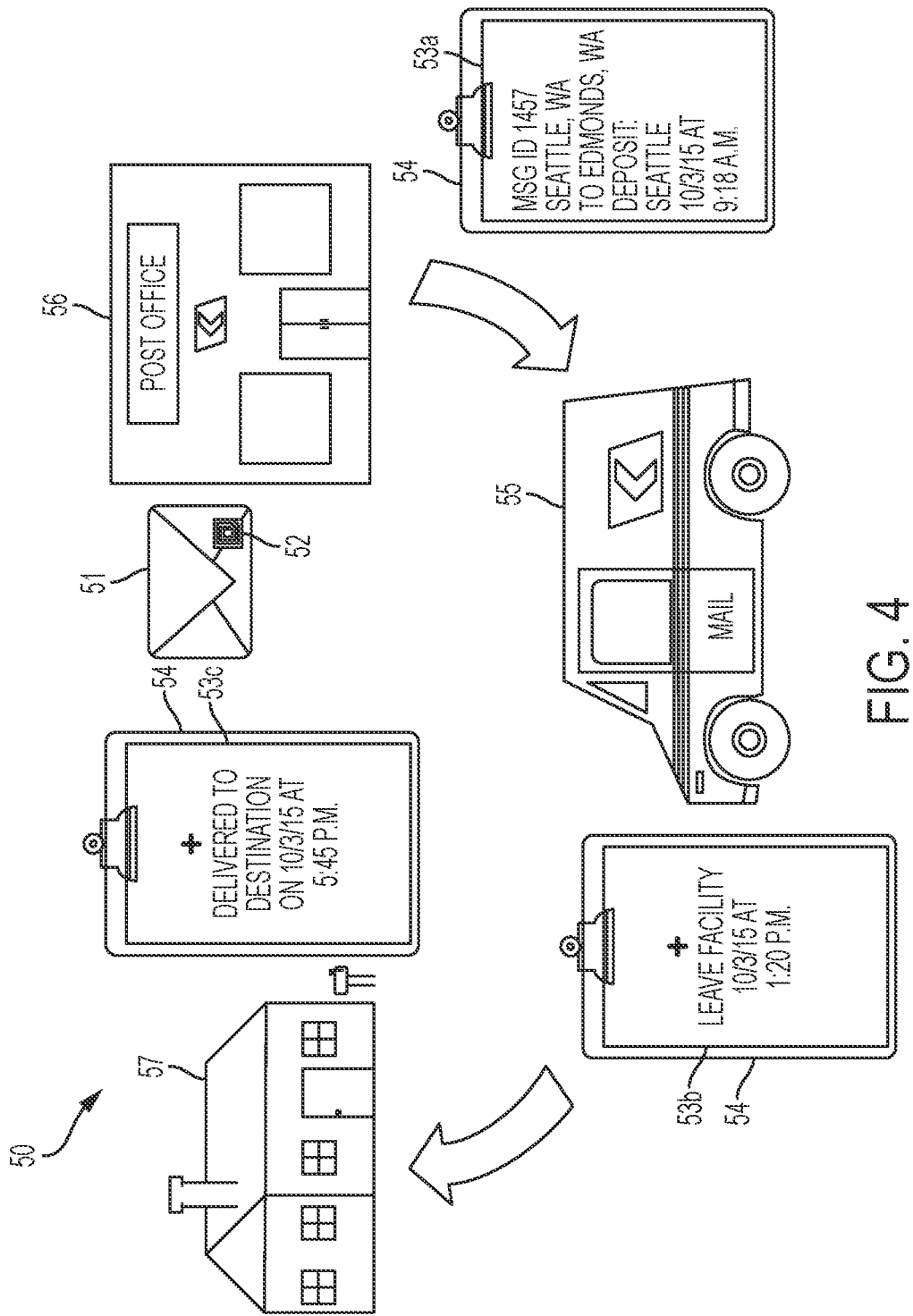
FIG. 4 is a flow diagram showing, by way of example, a process for object tracking and authentication.

In addition to individuals, objects and object-individual interactions can also be tracked using the real-time tracking system. FIG. 4 is a flow diagram showing, by way of example, a process 50 for object tracking and authentication. An object 51, such as a letter or other package, is selected for tracking and associated with a tracker 52. The tracker 52 can include a wireless device, RFID tag, or bar code, as well as other types of active and passive devices. The tracker 52 can be attached to the object, such as by taping, sticking, gluing, stapling, or otherwise affixing the tracker to the object. The sender of the object or another individual can attach the tracker to the object. For example, when the object is a letter for mailing, the sender can attach the tracker to the letter or an employee at a post office 56 can attach the tracker upon receipt of the letter from the sender.

Once the tracker is attached to the letter, registration of the object can occur by generating a record 54 for the object. The record 54 can include a name or identification number of the object, metadata of the object, and an identifier of the tracker. The object metadata can be dependent upon the object type and can include identifying information, as well as characteristics or traits of the object. For instance, for a letter being delivered, the metadata can include the letter size, weight, originating location, destination location, sender, and recipient. However, other types of objects may be associated with different types of metadata. For example, an organ being transferred from a donor to a recipient can be associated with metadata, including organ type, donor identification, donor sex and age, donor blood type, recipient identification, and recipient blood type. Other types of metadata are possible.

An interaction is logged for the object when the object tracker communicates with a tracking device of the responsible part and during transfer of the object from one responsible party to another. In this example, a first interaction of the object can occur when a first tracking device of a responsible party interfaces or communicates with the tracker attached to the object. For instance, when the sender provides the letter for mailing, such as to the postal worker at the post office 56, the tracking device of the postal worker can recognize the tracker by wirelessly reading or automatically communicating with the tracker.

In a further embodiment, readers can be placed in different locations, such as at an entrance or exit to the post office, or on a delivery truck to assist in tracking of the objects. When the tracker enters the predetermined range from the reader, an interaction between the tracker and reader can occur.

Data 53*a* about the interaction between the object and the postal worker can be recorded by the postal worker's tracking device and can also be transmitted to a data server for inclusion in the object's record 54 in real-time or on a periodic basis. The interaction data 53*a* recorded by the tracking device can include identification of the responsible party and the new responsible party to whom the object is being transferred, the time and date of interaction, and a condition of the object, as well as other information about the interaction. Tracking interactions can provide knowledge of the party responsible for an object, which can enable faster follow up if questions regarding the object arise. Further, interaction tracking can also provide authentication of the interaction by recording data about the parties or objects involved in the interaction, which can be compared with stored data to confirm or deny an authenticity of the interaction data.

While in the care of the postal worker, tracking of the object can continue via one or more interactions between the tracking device of the postal worker and the object tracker. For instance, the tracking device can interact with the tracker by requesting communication with or detecting a presence of the tracker attached to the letter continuously or on a periodic basis to ensure that the letter is still within a predetermined range of the postal worker. For example, passive RFID chips can be read by a tracking device within a range of about 1-2 feet, while active RFID chips can be read within a range of up to 300 feet. However, the use of smaller ranges help to prevent interference or cross-communication with other devices. By properly designing the tags and the antenna used for communication, a desired range can be achieved to address this issue. Unlike conventional bar code scanners, the tracking device of the delivery person can read all trackers within the predetermined range in a short amount of time, including the letter and other letters loaded onto the postal truck. The ability to read all the trackers saves large amounts of time generally required for individually and sequentially scanning bar codes associated with each package. Further, if the tracker is a wearable device, the tracking device and tracker can communicate wirelessly via Wi-Fi or Bluetooth, for example.

Tracking object interactions can be helpful to ensure that a particular object remains in the care of the responsible party and interactions can be initiated continually or on a periodic basis, such as at predetermined times or as requested. Data 53*a* collected from each interaction between the tracking device and the object tracker can be transmitted to a data server for inclusion in the record associated with the object in real-time or on a periodic basis. As described above, the interaction data 53*a* can include a time and location of the interaction, and a presence or condition of the object.

Object interaction tracking is also useful to determine a location of an object if lost during transit. For example, if the letter was not received by the recipient by a determined delivery date, the recipient or a postal employee can access the object record to determine when a presence of the letter was last identified based on the information obtained from each object interaction. The employee can then return to the last identified location of the letter in an attempt to locate the letter.

When the letter is ready to leave the post office 56, an interaction occurs between the postal worker and a delivery person, during which the letter is transferred onto a delivery truck 55 of the delivery person. The interaction includes communication between the tracking device of the postal worker and a tracking device associated with the delivery person during which data collected about the object by the postal worker's tracking device is transferred to the delivery person's tracking device. Further, information 53*b* about the interaction, as described above, can be recorded and stored on the tracking device of the delivery person, as well as added to the object's record 54.

While in the care of the delivery person, interactions between the delivery person and the letter can occur to ensure that the letter remains with the delivery person. Data about each interaction, including a date and time of the interaction, as well as a location, can be collected, stored, and transmitted to the data server. Each interaction between the delivery person and letter can occur continuously or periodically, such as randomly, as requested or at predetermined times.

Finally, at some point along the delivery person's route, the object is delivered to the intended recipient 57. Upon delivery, the tracking device of the delivery person can read the tracker of the letter, and information 53*c* about the interaction between the delivery person and letter can be recorded, including date, time, and location. The information 53*c* is then stored on the tracking device and can also be transmitted to a data server for inclusion in the record 54 for the letter. As the delivery person continues along his route, the letter will no longer be detected during any object tracking checks by the tracking device.

The interaction and entity data collected by each of the tracking devices can be used in real-time or at a later time to provide a history of an entity's interactions. The types of data collected can be dependent upon the tracking device of each responsible party. In one embodiment, the tracking devices worn by each party can include a proximity sensor that detects how far an individual or object is from the tracking device of the responsible party. Information obtained via the proximity sensor about a tracked entity can be stored in the entity's record. This information can later be used in court, such as for a chain of custody for a piece of evidence, or to provide information as to how closely the responsible party was watching the object. For example, a guard responsible for a prison inmate wears a tracking device that detects a proximity of the inmate from the guard while the inmate is in the guard's care. When the inmate is outside of a predetermined distance threshold from the guard, an alert can be provided. The alert can include one or more of a sound or alarm emitted from the guard's tracking device, displayed on the inmate's record, or a call or message to a third party.

Additionally, a tracking device can include a location tracker to determine whether the responsible party and entity to be tracked are travelling an approved or recommended path. Location information obtained about an entity can be stored in the entity's record. In one example, a responsible party transferring a high priced, valuable art piece may be delayed arriving to an intended destination. However, identifying a location of the tracker helps a third party determine why delivery of the art piece has been delayed and where the art piece is currently located. If the art piece is located along a predetermined route, no action may be taken. Yet, if the art piece is located in an unexpected place, an action can be taken, such as dispatching another individual to collect the art piece or calling the responsible party to confirm that no problems exist regarding the art piece.

Figure 5:
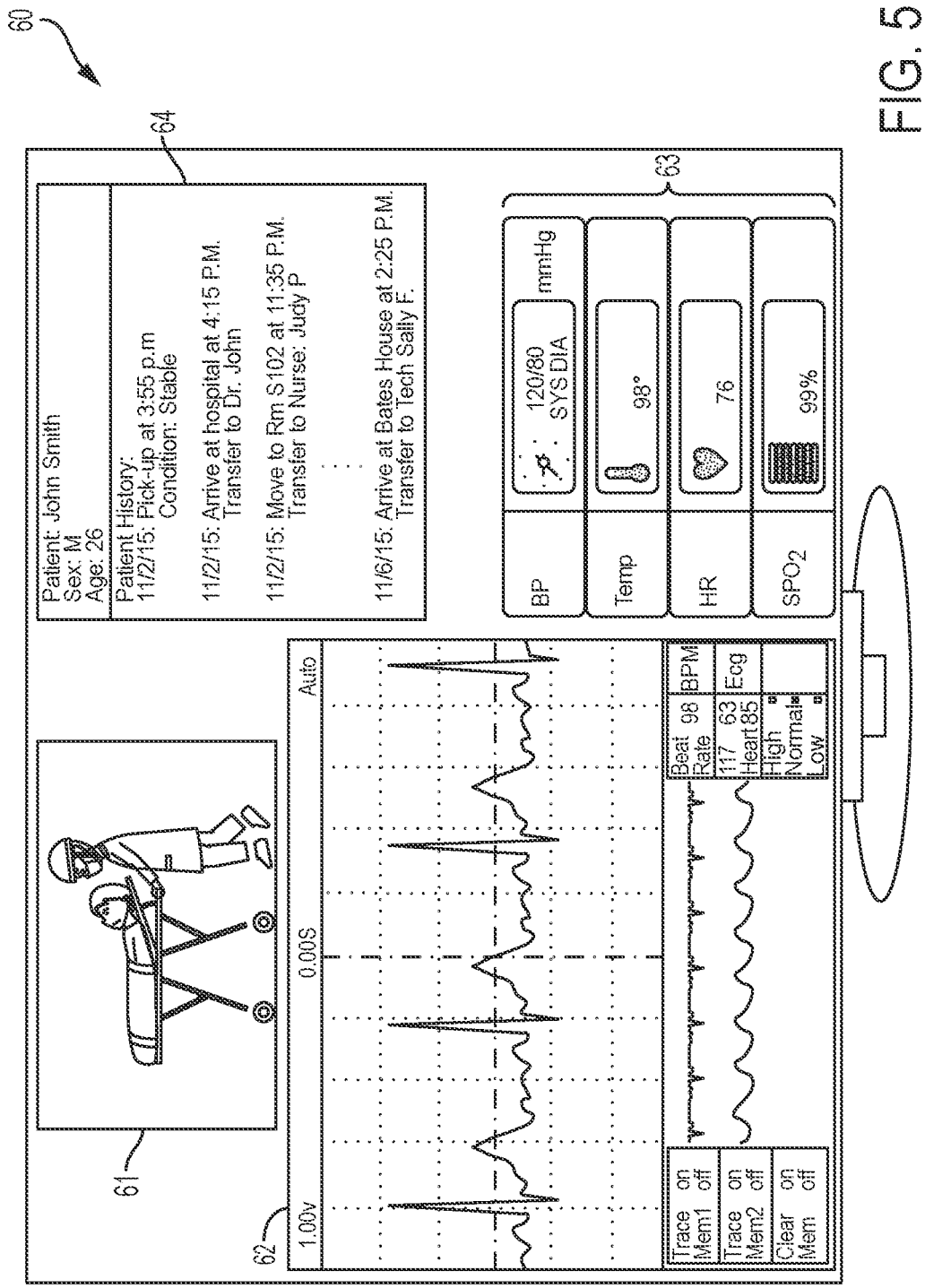
FIG. 5 is a block diagram showing, by way of example, a display of information for a tracked entity.

The interaction tracking data and entity tracking data can be stored in a record associated with the entity being tracked. The record can be accessed by a related party to provide a summary of the entity. FIG. 5 is a block diagram showing, by way of example, a display of a record 60 for a tracked entity. The record 60 can be accessed via a Website or web application. Alternatively, the record can be accessed from storage local or external to a computer on which the display is provided.

The type of information stored in a record can be dependent on the entity tracked. For instance, a record for a patient can include patient identification information, such as name, social security number, birthdate, age, sex, or, as well as vital measurements, check-ups, diagnosed disorders or illnesses, and prescribed medications. Interaction information collected for the patient can also be stored in the record and displayed. As described above, the interaction information can include identification of responsible parties, date and time of any interaction, location of interaction, and entity data collected from or about the patient, such as vital sign measurements, test results, location, and videos or voice recordings of the patient interactions. Other types of data for recording and storing regarding the patient and patient interactions are possible.

Further, the data stored in the entity records can be analyzed and displayed as graphs or provided in reports. For instance, a chain of custody, perhaps admissible in court for a piece of evidence, can be generated by accessing the interaction data stored in the record for the evidence and compiling a list of information that shows continuous possession by each individual that possessed the evidence beginning from seizure of the evidence until presentation in court. The list can include an identity of each individual responsible for the evidence, interactions between the responsible individual, including a date, time and location during which each interaction occurred and the parties involved in the interaction. Other types of information can be included in the chain of custody.

In a further example, a graph can be generated for an entity based on the collected data in the entity record. For example, a pie chart can be generated for a patient to determine how long each caretaker spent with the patient. Returning to the above example, with respect to FIG. 3, analysis of the data in the patient's record shows that the emergency room doctor spent half an hour with the patient in the emergency room, Dr. Jones spent 1 hour with the patient over a four day stay at the hospital, while Nurse Betty spent 6.5 hours with the patient over three eight hour shifts and Nurse Leslie spent 7.25 hours with the patient over four eight hour shifts, and Nurse Ben spent 10 hours with the patient over five eight hour shifts. The caretaker data can then be used with the caretaker data analyzed for other patients to determine a hiring need of a hospital, to determine whether patient interaction needs to be increases for one or more individuals, or to track employee efficiency and performance. Other reports or graphs, and uses of the reports or graphs are possible.

Further yet, a graph, such as a timeline of interactions for an entity can be generated based on the data stored in the entity record to provide an entity history. The timeline can be organized by date, time, or event. The date can include at least one of year, month, and day, depending on how much data the entity's record includes and an amount of detail required by a user. In one embodiment, if a user requires more detail, the user can zoom into each date or event to obtain further information.

Additionally, location data stored for an entity can be displayed on a map to show a location and route of the entity. Other displays of the recorded data can be displayed. Further, the interaction, entity, and location data collected by a tracking device or tracker can be displayed to a third party user in real-time.

Any reports, graphs, or other variations of the data can be stored with the record and displayed for a user accessing the record associated with a particular entity. Such request for access can be made via a computing device for display. Further, the data display can be interactive, such that the user can zoom in or out of the information, play videos or verbal recordings, add further notes directly to the record, or upload further videos or recordings.

Returning to the example provided with respect to FIG. 3, the display 60, as shown in FIG. 5, includes a video clip 61 of the patient being moved into the ambulance by the emergency responder. Data collected from the patient by the patient tracker or the tracking device of the emergency responder, such as vital sign measurements 62, 63, can also be displayed via numeric measurements, graphs, or icons. The display can also include a listing of interactions 64 recorded for the entity, including interactions between individuals responsible for the entity and between the entity and each responsible individual. Further, a time stamp associated with each item of data recorded can be used to correlate one or more data items. For example, a set of patient vital measurements associated with a time stamp can be correlated with a video of the patient that occurred at the same time based on a time stamp that occurred at the same time as or during the time stamp of the vital measurement collection. If the entity record includes large amounts of data, portions of the data can be displayed at a time, such as based on date, interaction, responsible party, or trip from a starting origin to an intended destination.

Although examples have been provided above, real-time tracking can be used for other types of entities, including children, elderly, particular types of diseases, including Alzheimer patients, sensitive documents in the financial or defense fields, artifacts, and other valuable items.

While the invention has been particularly shown and described as referenced to the embodiments thereof, those skilled in the art will understand that the foregoing and other changes in form and detail may be made therein without departing from the spirit and scope of the invention.

What is claimed is:

1. A computer-implemented system for entity tracking and identification, comprising:
   a tracker associated with an entity;
   a tracking device associated with an individual in custody of the entity and configured to attempt communication continuously with the tracker; and
   a server comprising a central processing unit, memory, an input port to receive data from one or more of the tracker and tracking device, and an output port, wherein the central processing unit is configured to:
      during one of the attempted communications, determine an absence of the tracker, comprising:
         identify a time of the attempted communication of the tracker by tracking device;
         apply a time threshold to the time for the attempted communication by the tracking device; and
         identify the absence of the tracker when no communication has been established with the tracking device within the time threshold;
      classify the entity as missing when the absence of the tracker is determined;
      collect data about the absence of the tracker and a lack of interaction between the tracker and the tracking device comprising an identity of the entity associated with the tracker; and
      store the collected data on the tracking device for transmitting to a data server for storage in a record for the entity.

2. A system according to claim 1, wherein the central processing unit classifies the tracker as in the presence of the individual when the attempted communications are successful.

3. A system according to claim 2, further comprising:
   a record generated for the entity and configured to store the successful attempted communications.

4. A system according to claim 3, wherein the records stores the absence of the tracker in the record.

5. A system according to claim 3, wherein the central processing unit determines a location of the tracker during each of the successful attempted communications stores the tracker locations in the record.

6. A system according to claim 5, wherein the central processing unit receives a request for a location of the entity and provides the location of the entity based on a most recent stored location of the tracker.

7. A system according to claim 6, further comprising:
   a map to display the location of the entity.

8. A system according to claim 1, wherein the central processing unit compares a location of the entity with a predetermined route of the entity and determines whether the entity is following the predetermined route.

9. A system according to claim 1, wherein the central processing unit collects from the tracker or the tracking device one or more of vital sign information from the entity, video of the entity, audio recordings, and test results.

10. A system according to claim 1, wherein the central processing unit collects further data regarding the absence of the tracker comprising at least one of an identity of the individual associated with the tracking device, a date and time of the communication attempt, and a location of the tracking device at a time of the communication attempt.

11. A computer-implemented method for entity tracking and identification, comprising:
    tracking a tracker associated with an entity;
    attempting communication continuously between the tracker and a tracking device associated with an individual in custody of the entity;
    during one of the attempted communications, determining an absence of the tracker, comprising:
       identifying a time of the attempted communication of the tracker by tracking device;
       applying a time threshold to the time for the attempted communication by the tracking device; and
       identifying the absence of the tracker when no communication has been established with the tracking device within the time threshold; and
    classifying the entity as missing when the absence of the tracker is determined;
    collecting data about the absence of the tracker and a lack of interaction between the tracker and the tracking device comprising an identity of the entity associated with the tracker; and
    storing the collected data on the tracking device for transmitting to a data server for storage in a record for the entity.

12. A method according to claim 11, further comprising:
    classifying the tracker as in the presence of the individual when the attempted communications are successful.

13. A method according to claim 12, further comprising:
    generating a record for the entity; and
    storing the successful attempted communications in the record.

14. A method according to claim 13, further comprising:
    storing the absence of the tracker in the record.

15. A method according to claim 12, further comprising:
    determining a location of the tracker during each of the successful attempted communications; and
    storing the tracker locations.

16. A method according to claim 15, further comprising:
    receiving a request for a location of the entity; and
    providing the location of the entity based on a most recent stored location of the tracker.

17. A method according to claim 16, further comprising:
    displaying the location of the entity on a map.

18. A method according to claim 11, further comprising:
    comparing a location of the entity with a predetermined route of the entity; and
    determining whether the entity is following the predetermined route.

19. A method according to claim 11, further comprising:
    collecting from the tracker or the tracking device one or more of vital sign information from the entity, video of the entity, audio recordings, and test results.

20. A method according to claim 11, further comprising:
    collecting further data regarding the absence of the tracker comprising at least one of an identity of the individual associated with the tracking device, a date and time of the communication attempt, and a location of the tracking device at a time of the communication attempt.

* * * * *